United States Patent
Kollias et al.

(10) Patent No.: US 6,728,560 B2
(45) Date of Patent: Apr. 27, 2004

(54) NON-INVASIVE TISSUE GLUCOSE LEVEL MONITORING

(75) Inventors: Nikiforos Kollias, Watertown, MA (US); Wei Dong Tian, West Roxbury, MA (US); Jenny E. Freeman, Chestnut Hill, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 10/084,984

(22) Filed: Feb. 28, 2002

(65) Prior Publication Data

US 2002/0082487 A1 Jun. 27, 2002

Related U.S. Application Data

(63) Continuation-in-part of application No. 09/287,486, filed on Apr. 6, 1999, now Pat. No. 6,505,059.
(60) Provisional application No. 60/080,794, filed on Apr. 6, 1998.

(51) Int. Cl.[7] ............................................. A61B 5/00
(52) U.S. Cl. ..................... 600/316; 600/317; 128/903
(58) Field of Search .................. 600/316, 319, 600/347, 365, 317; 128/903

(56) References Cited

U.S. PATENT DOCUMENTS

| | | |
|---|---|---|
| 3,837,339 A | 9/1974 | Aisenberg et al. |
| 4,206,755 A | 6/1980 | Klein |
| 4,515,165 A | 5/1985 | Carroll |
| 4,655,225 A | 4/1987 | Dähne et al. |
| 4,721,677 A | 1/1988 | Clark, Jr. .................... 435/291 |
| 4,866,644 A | 9/1989 | Shenk et al. |
| 4,979,509 A | 12/1990 | Hakky |
| 5,001,054 A | 3/1991 | Wagner ....................... 435/14 |
| 5,009,230 A | 4/1991 | Hutchinson |
| 5,070,874 A | 12/1991 | Barnes et al. |
| 5,101,814 A | 4/1992 | Palti |
| 5,115,137 A | 5/1992 | Andersson-Engels et al. ............ 250/461.2 |
| 5,140,989 A | 8/1992 | Lewis et al. |
| 5,190,041 A | 3/1993 | Palti |
| 5,202,424 A | 4/1993 | Vlassara et al. ............ 530/395 |

(List continued on next page.)

FOREIGN PATENT DOCUMENTS

| | | |
|---|---|---|
| EP | 0 063 431 A1 | 10/1982 |
| EP | 0 623 307 A1 | 11/1994 |
| EP | 0 663 591 A1 | 7/1995 |
| EP | 0 783 867 A1 | 7/1997 |
| GB | 2 300 045 A | 10/1996 |
| WO | WO 92/15008 A1 | 9/1992 |
| WO | WO 93/17621 A1 | 9/1993 |
| WO | WO 94/10901 A1 | 5/1994 |
| WO | WO 95/06431 A2 | 3/1995 |
| WO | WO 96/07889 A1 | 3/1996 |
| WO | WO 97/48331 A1 | 12/1997 |
| WO | WO 99/27848 A1 | 6/1999 |
| WO | WO 99/51142 | 10/1999 |

OTHER PUBLICATIONS

*Bruulsema et al., "Correlation Between Blood Glucose Concentration in Diabetics and Noninvasively Measured Tissue Optical Scattering Coefficient," Optics Letters, vol. 22, No. 3, Feb. 1, 1997.

(List continued on next page.)

Primary Examiner—Eric F. Winakur
(74) Attorney, Agent, or Firm—Kristofer E. Elbing

(57) ABSTRACT

Instruments and methods for performing non-invasive measurements of analyte concentrations and for monitoring, analyzing and regulating tissue status, such as tissue glucose levels.

8 Claims, 8 Drawing Sheets

U.S. PATENT DOCUMENTS

| | | | |
|---|---|---|---|
| 5,209,231 A | 5/1993 | Cote et al. | |
| 5,291,887 A | 3/1994 | Stanley et al. | |
| 5,313,941 A | 5/1994 | Braig et al. | |
| 5,318,023 A | 6/1994 | Vari et al. | |
| 5,341,805 A | 8/1994 | Stavridi et al. | |
| 5,342,789 A | 8/1994 | Chick et al. | 436/501 |
| 5,368,028 A | 11/1994 | Palti | |
| 5,370,114 A | 12/1994 | Wong et al. | |
| 5,372,135 A | 12/1994 | Mendelson et al. | |
| 5,377,676 A | 1/1995 | Vari et al. | |
| 5,379,764 A | 1/1995 | Barnes et al. | |
| 5,452,716 A | 9/1995 | Clift | |
| 5,459,677 A | 10/1995 | Kowalski et al. | |
| 5,460,177 A | 10/1995 | Purdy et al. | |
| 5,492,118 A | 2/1996 | Gratton et al. | |
| 5,497,772 A | 3/1996 | Schulman et al. | |
| 5,507,288 A | 4/1996 | Böcker et al. | |
| 5,515,847 A | 5/1996 | Braig et al. | |
| 5,517,313 A | 5/1996 | Colvin, Jr. | 356/417 |
| 5,533,509 A | 7/1996 | Koashi et al. | |
| 5,553,616 A | 9/1996 | Ham et al. | |
| 5,559,728 A | 9/1996 | Kowalski et al. | |
| 5,593,390 A | 1/1997 | Castellano et al. | 604/187 |
| 5,596,992 A | 1/1997 | Haaland et al. | |
| 5,601,079 A | 2/1997 | Wong et al. | |
| 5,657,754 A | 8/1997 | Rosencwaig | |
| 5,666,956 A | 9/1997 | Buchert | |
| 5,672,875 A | 9/1997 | Block et al. | 250/343 |
| 5,676,143 A | 10/1997 | Simonsen et al. | |
| 5,712,101 A | 1/1998 | Bucala | 435/7.1 |
| 5,713,353 A | 2/1998 | Castano | |
| 5,807,263 A | 9/1998 | Chance | 600/476 |
| 5,818,044 A | 10/1998 | Sodickson et al. | 250/339.06 |
| 5,818,048 A | 10/1998 | Sodickson et al. | 250/343 |
| 5,845,639 A | 12/1998 | Hochman et al. | |
| 5,850,623 A | 12/1998 | Carman, Jr. et al. | |
| 5,853,370 A | 12/1998 | Chance et al. | 600/473 |
| 5,857,462 A | 1/1999 | Thomas et al. | |
| 5,865,167 A | 2/1999 | Godik | |
| 5,865,829 A | 2/1999 | Kitajima | 606/3 |
| 5,879,294 A | 3/1999 | Anderson et al. | 600/310 |
| 5,902,235 A | 5/1999 | Lewis et al. | 600/323 |
| 5,921,926 A | 7/1999 | Rolland et al. | 600/407 |
| 5,986,770 A | 11/1999 | Hein et al. | 356/446 |
| 5,999,836 A | 12/1999 | Nelson et al. | 600/407 |
| 6,002,953 A | 12/1999 | Block | 600/316 |
| 6,016,435 A | 1/2000 | Maruo et al. | 600/316 |
| 6,028,311 A | 2/2000 | Sodickson et al. | 250/343 |
| 6,032,070 A | 2/2000 | Flock et al. | 600/473 |
| 6,044,285 A | 3/2000 | Chaiken et al. | 600/316 |
| 6,049,727 A | 4/2000 | Crothall | |
| 6,064,065 A | 5/2000 | Block et al. | 250/341.3 |
| 6,078,828 A | 6/2000 | Yasuda et al. | |
| 6,088,605 A | 7/2000 | Griffith et al. | 600/316 |
| 6,124,597 A | 9/2000 | Shehada et al. | |
| 6,172,743 B1 | 1/2001 | Kley et al. | |
| 6,175,752 B1 * | 1/2001 | Say et al. | 600/345 |
| 6,222,189 B1 | 4/2001 | Misner et al. | 250/341.1 |
| 6,232,609 B1 | 5/2001 | Snyder et al. | |
| 6,505,059 B1 | 1/2003 | Kollias et al. | |
| 2002/0143243 A1 | 10/2002 | Georgakoudi et al. | |

OTHER PUBLICATIONS

*Klonoff, "Noninvasive Blood Glucose Monitoring," Diabetes Care, vol. 20, No. 3, Mar. 1997.

*Kohl et al., "Influence of Glucose Concentration on Light Scattering in Tissue–Simulating Phantoms," Optics Letters, vol. 19, No. 24, Dec. 15, 1994.

*Kollias et al., "Endogenous Skin Fluorescence Includes Bands that may Serve as Quantitative Markers of Aging and Photoaging," Journal of Investigative Dermatology, vol. 111, No. 5, Nov. 1998.

*Maier et al., "Possible Correlation Between Blood Glucose Concentration and the Reduced Scattering Coefficient of Tissues in the Near Infrared," Optics Letters, vol. 19, No. 24, Dec. 15, 1994.

*Newsedge Corporation, "Cygnus Completes Pre–Market Application for the GlucoWatch ® Monitor", Jun. 3, 1999.

*Qu and Wilson, "Monte Carlo Modeling Studies of the Effect of Physiological Factors and Other Analytes on the Determination of Glucose Concentration In Vivo by Near Infrared Optical Absorption and Scattering Measurements," Journal of Biomedical Optics, vol. 2, No. 3, Jul. 1997.

*Rolinksi et al., "Near Infra–red Assay for Glucose Determination," International Society for Optical Engineering, Technical Abstract Digest from the International Symposium on Biomedical Optics, San Jose, CA, Jan. 23, 1999.

*Sannes, "The Outlook for Noninvasive and Minimally Invasive Glucose Testing," Decision Resources, Inc., Nov. 1998.

*Schwartz, Jon A et al., "Diagnostic Potential of Laser–Induced Autofluorescence Emission in Brain Tissue," Journal of Korean Medical Science, vol. 12, No. 2, Apr. 1997, pp. 135–142.

*Wynant and Chenault, "Special Issue on Non–Invasive Glucose Monitoring with Optical Techniques," Leos Newsletter, Apr. 1998.

Alam, M. Kathleen et al. "Characterization of pH Variation in Lysed Blood by Near–Infrared Spectroscopy," Applied Spectroscopy, vol. 52, No. 3, pp. 393–399,1998.

Alam, M. Kathleen et al. "Measurement of pH in Whole Blood by Near–Infrared Spectroscopy," Applied Spectroscopy, vol. 53, No. 3, pp. 316–323, 1998.

Diffee, John T., "Tobacco Analysis by NIR Spectroscopy," R.J. Reynolds Tobacco Company, Winston–Salem, North Carolina, 1992.

Monnier, V.M. et al. "Skin Collagen Glycation, Glucoxidation, and Crosslinking Are Lower in Subjects with Long–Term Intesive Versus Conventional Therapy of Type I Diabetes," Diabetes 48, pp. 870–880, 1999.

Wang et al., "Multivariate Instrument Standardization," Anal. Chem., vol. 63, pp. 2750–2756, 1991.

Wang et al. "Improvement of Multivariate Calibration through Instrument Standardization," Anal. Chem., vol. 64, pp. 562–564, 1992.

Wang et al. "Additive Background Correction in Multivariate Instrument Standardization," Anal. Chem., vol. 67, pp. 2379–2385, 1995.

* cited by examiner

NON-INVASIVE TISSUE GLUCOSE LEVEL MONITORING

REFERENCE TO RELATED APPLICATIONS

This patent application is a divisional application Ser. No. 09/287,486, filed Apr. 6, 1999, which claims the benefit under 35 U.S.C. § (e) of provisional application Ser. No. 60/080,794, filed Apr. 6, 1998, which are both entitled Non-invasive Tissue Glucose Level Monitoring and herein incorporated by reference.

FIELD OF THE INVENTION

This invention relates to instruments and methods for performing non-invasive measurements of analyte concentrations and for monitoring, analyzing and regulating tissue status, such as tissue glucose levels.

BACKGROUND OF THE INVENTION

Diabetes is a chronic life threatening disease for which there is presently no cure. It is the fourth leading cause of death by disease in the U.S. and at least 90 million people worldwide are estimated to be diabetic. Diabetes is a disease in which the body does not properly produce or respond to insulin. The high glucose levels that can result from this affliction can cause severe damage to vital organs, such as the heart, eyes and kidneys.

Type I diabetes juvenile diabetes or insulin-dependent diabetes mellitus) is the most severe form of the disease comprising approximately 10% of the diabetes cases in the United States. Type I diabetics must receive daily injections of insulin in order to sustain life. Type II diabetes, (adult onset diabetes or non-insulin dependent diabetes mellitus) comprises the other 90% of the diabetes cases. Type II diabetes is often manageable with dietary modifications and physical exercise, but may still require treatment with insulin or other medications. Because the management of glucose to near normal levels can prevent the onset and the progression of complications of diabetes, persons afflicted with either form of the disease are instructed to monitor their blood glucose level in order to assure that the appropriate level is achieved and maintained.

Traditional methods of monitoring the blood glucose level of an individual require that blood be withdrawn. This method is painful, inconvenient, costly and poses the risk of infection. Another glucose measuring method involves urine analysis, which, aside from being inconvenient, may not reflect the current status of the patient's blood glucose because glucose appears in the urine only after a significant period of elevated levels of blood glucose. An additional inconvenience of these traditional methods is that they require testing supplies such as collection receptacles, syringes, glucose measuring devices and test kits. Although disposable supplies have been developed, they are costly and can require special methods for disposal.

Many attempts have been made to develop a painless, non-invasive external device to monitor glucose levels. Various approaches have included electrochemical and spectroscopic technologies, such as near-infrared spectroscopy and Raman Spectroscopy. Despite extensive efforts, however, none of these methods appears to have yielded a non-invasive device or method for the in vivo measurement of glucose that is sufficiently accurate, reliable, convenient and cost-effective for routine use.

SUMMARY OF THE INVENTION

The invention overcomes problems and disadvantages associated with current strategies and designs and provides new instruments and methods for monitoring, analyzing and regulating in vivo glucose levels or other analyte levels in an individual.

In one general aspect, the invention features a non-invasive glucose monitoring instrument useful in vivo. The instrument may comprise a radiation source capable of directing radiation to a portion of the exterior or interior surface of a patient. That surface may be a mucosal area such as the gums and other mucosal areas, the eyeballs and surrounding areas such as the eyelids and, preferably, the skin. The source emits radiation at a wavelength that excites a target within the patient such that the excited target provides a glucose level indication of the patient. A glucose level indication is a quantitative or relative measurement that correlates with the blood glucose content or concentration of the patient. The instrument may further comprise a radiation detector positioned to receive radiation emitted from the excited target, and a processing circuit operatively connected to the radiation detector that translates emitted radiation to a measurable signal to obtain the glucose level indication. The target is not glucose itself, but a molecular component of the patient such as, for example, a component of skin or other tissue, that reflects or is sensitive to glucose concentration, such as tryptophan or collagen cross-links. Suitable targets are structural components, and compounds and molecules that reflect alterations in the environment of matrix components of the tissue and are sensitive to or correlate with tissue glucose concentration. The target provides an emitted fluorescence signal that is related to the patient's blood glucose level. The radiation detector is responsive to the emission band of the target or species in the skin. Preferably the radiation is ultraviolet radiation or light. The emitted radiation is preferably fluorescence radiation from the excitation of the non-glucose target. The instrument may further include means for measuring scattering re-emitted from the irradiated skin. The radiation emitted from the excited target and signal therefrom correlates with the blood glucose of the patient.

Another aspect of the invention relates to an instrument for assessing changes in the superficial structural matrix of the skin or other tissue of a patient comprising means for measuring fluorescence, and means for measuring scattering.

Another aspect of the invention relates to an instrument for assessing changes in the environment of matrix components of the skin or other tissue of a patient comprising means for measuring fluorescence, and means for measuring scattering. Preferred embodiments further include means for combining signals from the means for measuring fluorescence and the means for measuring scattering.

Another aspect of the invention relates to a non-invasive method of detecting or assessing a glucose level comprising exciting a target that, in an excited state, is indicative of the glucose level of a patient, detecting the amount of radiation emitted by the target, and determining the glucose level of the patient from the amount of radiation detected. The target is preferably a molecular species in the skin. Preferred targets are tryptophan or a matrix target, like PDCCL, which are excited by ultraviolet radiation and act as bioamplifiers or bioreporters. Targets may be structural matrix or cellular components. Suitable targets reflect alterations within the environment of matrix components of the skin or other tissue and act as bioamplifiers or bioreporters when excited with ultraviolet radiation.

Still another aspect of the invention relates to a non-invasive method of assessing a change in the superficial structural matrix of a tissue, or a change in the environment of matrix components, comprising exposing the tissue to radiation at a first wavelength, detecting an amount of fluorescence emitted by exposed tissue, exposing the tissue to radiation of a second wavelength, detecting an amount of scattering re-emitted from the exposed tissue, and deriving an indication representative of the change in the superficial structural matrix of the tissue, or a change in tissue matrix components or their environment, based on of the amount of fluorescence detected and the amount of scattering detected.

Other objects and advantages of the invention are set forth in part in the description which follows, and in part, will be obvious from this description, or may be learned from the practice of the invention.

DETAILED DESCRIPTION OF ILLUSTRATIVE EMBODIMENTS

Figure 1:
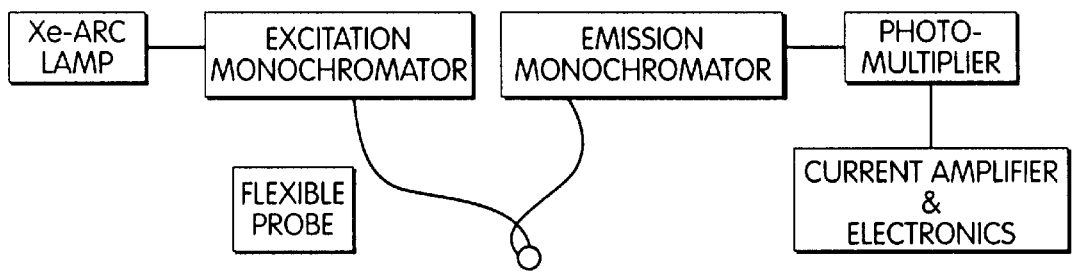
FIG. 1 A multipurpose skin spectrometer that provides data specifically relevant to signals correlating with blood glucose.

As embodied and broadly described herein, the present invention relates to devices and methods for quantitating, trending and/or reporting an analyte, such as blood glucose, to devices and methods for monitoring and regulating in vivo glucose levels, and to devices and methods for evaluating the superficial structural matrix or cellular components of a tissue.

It has been discovered that by measuring fluorescence following irradiation of a tissue surface of a patient, such as the patient's skin, and by optionally assessing scattering, the glucose level of a patient can be evaluated. Evaluation according to the invention is based on the surprising discovery that the quantum efficiency of fluorescence of a responsive target within the skin is transiently affected by the irradiation and can be correlated to the ambient glucose content. Long-term interaction between diabetes, collagen and other species has been previously observed (V. M. Monnier et al., Diabetes 37:867–872, 1988). However, a reversible component of this interaction that correlates with blood glucose levels and possibly depends on the glucose level in the environment of collagen and other targets has previously gone unnoticed. More specifically, although glucose itself does not fluoresce to any significant degree, when the blood glucose level of a patient changes, the quantum efficiency of fluorescence of a target such as, for example, pepsin-digestible collagen cross links (PDCCL), also changes. This change may be due, in part, to the direct and indirect effects of the relative presence of glucose or other molecules on the environment of target molecules and structures. That presence induces a reversible change in the quantum efficiency of fluorescence production by the target which can be detected and analyzed. Glucose molecules in the environment may be covalently or noncovalently coupled to the target (glycosylated collagen), or simply free in the immediate vicinity of the target. Targets may be in the dermal matrix, in the epidermal matrix, or in cells or the immediate vicinity of cells associated with the either the dermis or the epidermis. In this regard, the invention may also be used to directly assess the amount or degree of advanced glycation end products that exist in an area of the body such as, for example, in vessels, arteries or organs.

A fluorescent signal originating from dermal collagen cross links has been identified, which signal slowly increases with aging and is also sensitive to transient exposure to ultraviolet radiation. PDCCL fluoresces following excitation at 335–340 nm, with the emission maximum at 390 nm (N. Kollias et al., Journal of Investigative Dermatology, 111:776–81 1998). The fluorescent signal decreases monotonically with a single UV exposure, but recovers within hours. With multiple exposures, the effects appear cumulative, and recovery takes weeks. However, it has been discovered that transient changes in the environment of these collagen cross links causes significant and transient alterations in their fluorescence which can be tightly correlated with blood glucose determinations.

Targets in the environment of matrix components, such as collagen cross links serve as bioamplifiers or bioreporters of ambient glucose concentrations and, thus, constitute a novel and sensitive means of non-invasively assessing glucose in real time. Advantages of this methodology include a large change in signal level for a relatively small change in collagen structure or matrix environment. The method is also unhampered by absorption from competing species in the general area. In addition, there are only a few fluorophores which makes signal analysis easier. Further, detector sensitivity is generally excellent and instrumentation and optical components, all of which are commercially available, are potentially simpler and less expensive than those used for infrared measurements. Also, given the robust signals and signal to noise ratios observed, there is potentially less of a need to resort to complex algorithmic and chemometric analyses.

Accordingly, one aspect of the present invention is related to a non-invasive in vivo glucose monitoring instrument that determines glucose levels or changes in glucose levels by measuring fluorescence of the skin following excitation of one of these targets or species. Specifically, fluorescence signals obtained following irradiation of skin or other tissue can be correlated with glucose levels, or changes in glucose levels, by measuring fluorescence following excitation of targets or species within the environment of the matrix components. Preferred targets are structural matrix components such as PDCCL. Another preferred target is epidermal tryptophan which, like other targets, may be bound to other compounds or structures, and intracellularly or extracellularly localized. Other useful matrix targets for excitation include collagenase-digestible cross links, elastin cross links, glycosaminoglycans, glycated collagen and glycosylated substances in a tissue. These targets may also be referred to as biosensors as they are biological substances that detectably change in response to glucose content, or bioamplifiers as they may amplify a signal indicative of systemic glucose levels.

A non-invasive glucose monitoring instrument according to one aspect of the invention includes a radiation source capable of directing radiation to a portion of the surface of the skin (or other tissue) of a patient. The source emits radiation at a wavelength that excites a target of species in the tissue that can be correlated with blood glucose content, such that the excited target provides a glucose level indication of the patient. In a preferred embodiment, the target is a molecule other than glucose, and most preferably is a structural matrix component such as, for example, collagen cross-links. Alternatively, the target may be tryptophan. When the target being detected is cross-linked collagen, the ultraviolet radiation source is preferably operative to irradiate at approximately 330–345 nanometers, and the ultraviolet detector is sensitive to emitted wavelengths in the range of 370–410 nanometers, more preferably, 380–400 nanometers and, most preferably, 390 nanometers. As noted, another useful target whose change in emission may be detectable is tryptophan. When the target being detected is tryptophan, the ultraviolet radiation source is preferably operative to irradiate at approximately 285–305 nanometers, more preferably at approximately 295 nanometers, and the ultraviolet detector is preferably sensitive to emitted wavelengths in the range of 315–420 nanometers, more preferably 340–360 nanometers, and most preferably, 345 nanometers. The radiation emitted by the target correlates with the glucose level of the patient. The spectral information can be converted into a number correlative to standard blood glucose determinations.

The instrument further comprises a radiation detector positioned to receive radiation emitted from an excited target. The instrument further includes a processing circuit operatively connected to the radiation detector and operative to translate a level of emitted radiation into a measurable signal that is representative of or may be correlated with the blood glucose level. Preferably, the radiation source is ultraviolet light. In a preferred embodiment the radiation source may comprise a flexible-fiber optic arm or probe that directs said radiation to the target. The probe may comprise a glass or quartz fiber and may be flexible and easily manipulated to examine a site anywhere on the patient's skin. The portion of skin irradiated may be less than about 1 square cm, and more preferably is about 0.2 square cm. Preferably, the portion is a site which is most easily measurable on the patient such as on the arm or leg. Differences in pigmentation between different areas of the body as well as different patients can be factored or eliminated through selection of control input, and overcome.

The instrument may further comprise a display such as, for example, a visual, auditory or sensory display operatively connected to the processing circuit and operative to display the glucose level indication. Optionally, this data may be analyzed and transmitted to a pump or other servo mechanism responsive to the processing circuit. The pump is incorporated into the system such that the pump administers insulin or other medication to the patient at a rate that corresponds to the glucose level signal.

Referring to FIG. 1, an embodiment of the glucose monitor of the invention includes a Xenon arc (Xe-arc) lamp, double excitation and emission monochromators, a photomultiplier device, a simple current amplifier and a flexible probe. The probe may comprise fiber optic bundles which allow convenient evaluation of living systems. This embodiment can take the form of a multipurpose skin spectrometer or it may be modified to create a unit optimized to provide data specifically relevant to signals correlating with blood glucose. One advantage of utilizing fluorescent excitation spectra compared to fluorescence emission spectra is that the former are similar to absorption spectra, which aids in the separation and identification of the individual fluorophores in a complex spectrum. Although other components can be substituted for the elements in this embodiment, a Xe-arc in combination with an excitation monochromator, avoids the major constraint of laser sources, namely the limited number of excitation wavelengths.

Optionally, other types of sources, such as a diode laser, coupled with enhanced spectral analysis algorithms optimized for the collagen cross links may be used. These algorithms may also incorporate variables such as skin type, age, exposure, etc., all of which are analyzed during testing. Hardware modifications and calibrations may be incorporated to take into account these and other variables. Specific algorithms and software may be embedded into a dedicated processor. For example, one design may comprise a night hypo/hyperglycemia monitoring instrument which is programmed to alarm by trending analysis parameters that correlate with significant changes in blood glucose. Alternatively, monitoring could be performed with a transportable fiber-based fluorescence spectrophotometer with double monochromators, both on the excitation and emission paths. This allows the evaluation of different subsets of collagen cross links and tryptophan signals as well as allowing the estimation of epidermal melanin pigmentation or other tissue pigments. Optimized instruments may duplicate and incorporate the functionality and data processing requirements incorporated from appropriate studies.

Another embodiment uses a fiber-based fluorescence spectrometer with two double monochromators and a high intensity excitation light source (350 W Xe-arc). The double monochromator design minimizes stray light, which tends to be high because of the high level of light scattering by the tissues. The probe is preferably a fiber optic device that allows collection of data from different skin sites on the body. Probe design is optimized to permit ease of use and reproducibility. Optimization of light sources, filters and software can be designed to perform three scans that maximize the collagen fluorescence signals. One scan is preferably 250–360 nm on the excitation band and 380 nm on the emission. The second scan is preferably 250–400 nm on the excitation and 420 nm on the emission. The third scan is preferably 360–480 nm on the excitation and 500 nm on the emission. This provides information on PDCCL (340/390 nm), the collagenase digestible collagen crosslinks (370/460 nm) and the collagen/elastin crosslinks (420/500 nm), among other species. The system may also provide data on tryptophan, an epidermal fluorophore having an excitation wavelength of 290–300 nm and an emission wavelength of 340–360 nm, among other species. Devices may be small and lightweight desktop units useful in health care provider settings. A remote probe may be connected to the system through a flexible fiber optic bundle. Data output may consist of a reporting of a quantitative number that correlates with blood glucose readings, along with spectral data, which may be displayed on a separate small I/O terminal or laptop computer. The software further contains diagnostic overlay capabilities.

Another device allows monitoring of glucose levels, by providing spectral information reflective of glucose levels, on a continuous or repetitive basis. In one embodiment, this would be used throughout the night with a built-in alarm, to alert the patient to abnormal decreases or increases in glucose levels. The unit, which may be the size of a clock radio, can have a fiber optic cable to connect to the patient, similar to existing apnea monitors and pulse oxymeters. Another portable device may be placed in contact with the skin for periodic momentary glucose readings. It may have an LCD readout for glucose levels, memory to store several hundred glucose readings and a data output to download stored data.

An alarm may be operationally coupled to the processing circuit such that the alarm is activated when the glucose level indication exceeds a first predetermined value (such as 200 gm/l), falls below a second predetermined value (such as 70 gm/ml), or varies more than 20% from a third predetermined value (such as the previously measured level or a baseline level determined for the patient). Alternately, the alarm may be triggered in response to a more complex algorithmic analysis of data or based on evaluation by trending analysis over time.

The instrument may further comprise a normalizing detector responsive to another target in the tissue, such that the processing circuit is responsive to the normalizing detector to normalize the glucose level indication. For example, a current or latest glucose level signal may be normalized by comparing it to a previously determined glucose level signal which has been calibrated by comparing it directly with a conventionally determined blood glucose level. Alternatively, normalization may involve comparison of emissions from the same target but at another wavelength, comparison of emissions from a non-target such as glucose or another structural or circulating component of the body, or simply taking a reading from another skin site. Normalization may also be performed by comparison to similar data from another point or points in time taken from the same individual, or utilizing a stored database or spectral library. Normalizing may alternately comprise obtaining a baseline signal before any prolonged activity where continual measurements would be difficult such as, for example, before driving or sleeping, and watching for changes or trends of changes. The previously determined glucose level signal may also be compared with a level assessed from a simultaneously drawn blood sample. In addition, scattering evaluation may be factored into the normalizing process.

The instrument may optionally comprise means for measuring scattering re-emitted from the tissue. As discussed below, the means for measuring scattering may comprise a skin illuminating means that emits radiation at an angle greater than 60 degrees to said target or it may comprise a skin or tissue illuminating means which emits radiation at between about 330 to 420 nm. Re-emitted radiation is then collected and analyzed.

The instrument may include a portable housing in which the radiation source, the radiation detector and the processing circuit are disposed. The instrument may include a battery compartment disposed in the housing and a pair of battery contacts operatively connected to the ultraviolet radiation source, the ultraviolet radiation detector, and the processor. Data can be electronically recorded, stored or downloaded for later review or analysis. The instrument may further comprise attachment means for attaching the radiation source, a portion of, or all of the device to the patient. The portable housing, the ultraviolet radiation source, the ultraviolet radiation detector, and the processor may be designed so that they weigh in combination less than 3 kilograms, more preferably less than 1 kilogram, and most preferably, less than 0.5 kilograms. The instrument may optionally include an attachment mechanism for attaching the housing to the patient. Alternately, the instrument can be miniaturized; in such an embodiment, a microprocessor is incorporated onto a dermal patch, which may be operatively connected to other devices that provide input directly to a pump or other biodelivery system, such as a transmucosal or inhalational system, which may deliver insulin or other appropriate medication to the patient.

The instrument may also be constructed using small components composed of inexpensive, possibly recyclable materials such as plastics and paper, so that the entire instrument or a significant portion is disposable. For example, the entire device can be incorporated into a patch worn anywhere on the body and secured with adhesive tape, hook-and-loop fastener or another suitable means. After expiration or depletion of an integral battery, the patch can be safely and easily disposed of and a new patch secured. Such instruments weigh less than 1 kg, preferably less than 0.5 kg and more preferably less than 0.1 kg.

The processing circuit is preferably operative to translate the level of detected radiation into a measurable glucose level signal that is indicative of the glucose level in the tissue. The signal may be directly evaluated, or it may be compared to stored reference profiles, to provide an indication of changes from previous levels or trends in the patient's glucose level. Although a preferred embodiment measures radiation or fluorescence following irradiation of the skin, the present invention can also be used to assess glucose levels by evaluation of other tissues. For instance, glucose levels may be assessed in accordance with the present invention by detecting radiation or fluorescence following irradiation of the surface of other tissues, such as mucous membranes, or irradiation of the mucosa, submucosa or serosa of any organ.

Another aspect of the invention relates to a non-invasive method of detecting a glucose concentration or level in vivo comprising the steps of exciting a target in the skin or other tissue, preferably using ultraviolet radiation, that is sensitive to the patient's tissue glucose content and is indicative of the glucose level of the patient, detecting an amount of radiation or fluorescence emitted by the target, and deriving an indication representative of or which correlates with a current blood glucose level based on the amount of radiation or fluorescence detected. Preferably, the target is a matrix target such as collagen cross links. Alternatively, the target may be tryptophan. The method may optionally include the step of determining whether to take steps to adjust the patient's glucose level in response to the derived glucose level, followed by the step of administering insulin or another pharmaceutical composition in response thereto. The method may include any one or more of the steps of reporting the information to the patient, recommending a dosage, or administering the composition, such as insulin, to the patient in response to the indication derived. The step of administering may be performed by using a syringe, a pump or another suitable biodelivery system, mechanical or chemical, which may be implanted or external to the body. The method may also include the step of displaying a glucose level indication related to the indication derived or providing a warning to the patient. The method may further include the step of normalizing the glucose level indication derived in the step of deriving. The steps of exciting, detecting, and deriving may be performed continuously or at any appropriate interval, for example, by the minute, hourly, daily or every other day for the same patient and over a period of days, weeks, months or years.

Optionally, the method may include actuating an alarm in response to the glucose level when the glucose level exceeds a predetermined first level, falls below a predetermined second level or varies more than a set percentage, such as for example, 10%, 20%, 30%, 50% or 100% or more from a predetermined third level or changes in such a way that meets criteria of a specifically designed algorithm. The method may further comprise the step of measuring scattering re-emitted from the skin or irradiated tissue surface and utilizing the resulting data to initiate or assist in actuating a process aimed at adjusting the glucose level.

Instruments according to the invention are advantageous in that they provide information relative to blood glucose and permit glucose levels to be evaluated noninvasively. Such non-invasive instruments allow people with diabetes to monitor glucose levels without the pain, inconvenience, and risk of infection associated with obtaining a blood sample. By making monitoring safer and more convenient, people with diabetes can monitor their glucose levels more frequently and therefore control levels more closely. Safer and more convenient glucose level monitoring reduces the likelihood of measurements being skipped.

Furthermore, by coupling the instrument according to the invention with a pump or other device which can deliver insulin or other therapeutic agent to the patient, using a transmitter, or other suitable communication device, such that the pump or device is responsive to the glucose signal, even finer automatic glucose level monitoring may be achievable. For example, the transmitter may remotely transmit the signal to a pump, such as a servo pump, having a receiver responsive to the transmitted signal. The pump is preferably responsive to information derived from or analysis of the spectral signal. The pump may then provide insulin or other appropriate medication to the patient. Alternately, or in addition, the information may be sent to a remote monitor.

As will be clear to those of skill in the art, the instruments and methods of the present invention can also be used in forensic applications, to allow the non-invasive and non-destructive assessment of forensic tissues. In addition, the instruments and methods may be used to detect and diagnose diabetes, monitor the progression of diabetes, and detect and monitor other disorders involving hyper or hypoglycemia or abnormal blood sugar metabolism. Although the term in vivo is used to refer to living material, it is intended herein to encompass forensic applications as well.

Figure 2:
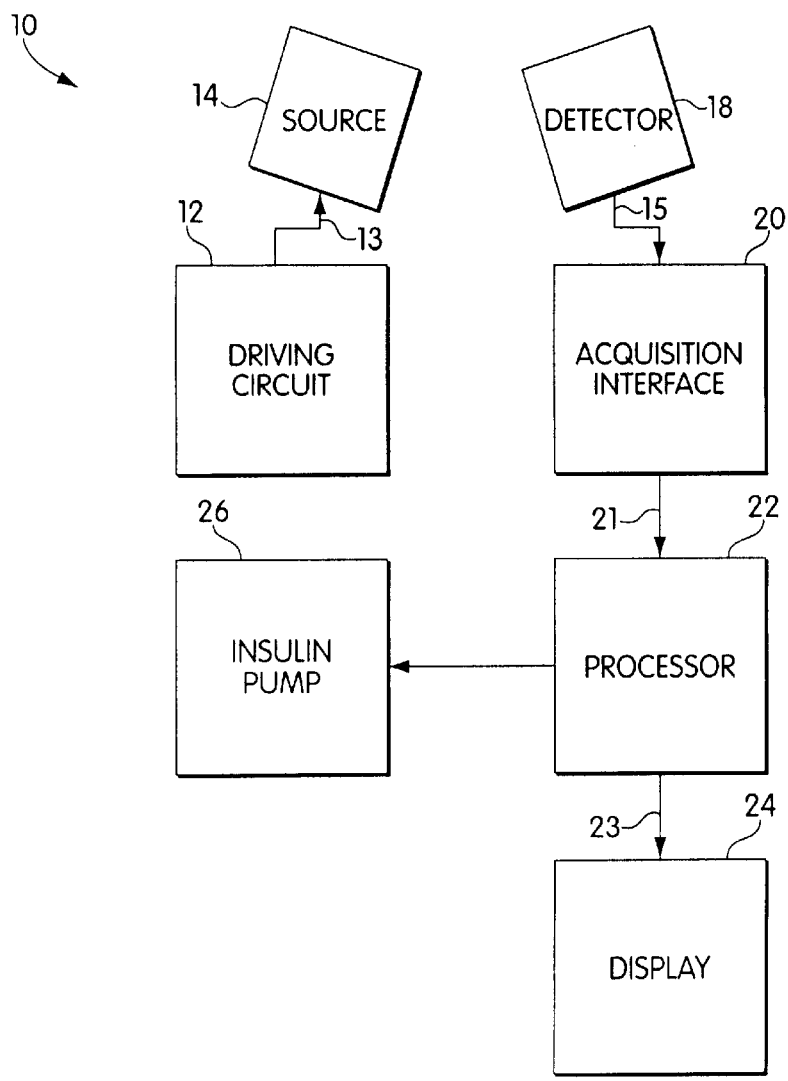
FIG. 2 Block diagram of one embodiment of a glucose level monitoring instrument.

Another embodiment of the present invention is depicted in FIG. 2, which depicts a glucose level monitoring instrument 10 including source driving circuit 12 having an output provided to an input 13 of a source 14. Source driving circuit 12 controls the illumination, provided by source 14. Source driving circuit 12 may take a number of forms, depending on the nature of the source and the acquisition. Examples include a regulated power supply or a pulsed modulator.

Source 14 preferably comprises an ultraviolet light source, such as a continuous mercury lamp, a pulsed or continuous xenon flash lamp, or a suitable laser. Useful lasers include, but are not limited to, nitrogen lasers, OPO (tunable laser) and Nd YAG pump devices. The output of source 14 may be filtered to restrict illumination to within excitation bands of interest. Its intensity (and pulse width if applicable) is preferably set at a level that minimizes exposure while optimizing signal-to-noise considerations. It is also possible to irradiate the sample with two or more short (e.g. femtosecond) pulses of multiphoton light having a wavelength two or more times longer than the wavelength of interest, such that the radiation penetrates to a different degree or depth. The source is positioned to illuminate an area of interest on the patient's skin 16.

Glucose level monitoring instrument 10 also includes a detector 18 that is sensitive to ultraviolet light emitted by the species that is excited by the source 14. The detector has an output 15 operatively connected to an input of an acquisition interface 20, which may be an analog-to-digital converter with an analog input operatively connected to the detector output. A digital output port 21 of the acquisition interface is operatively connected to processor 22.

Processor 22 is operative to convert the digital detector output signal into a glucose level signal. The processor may perform this conversion by applying various signal processing operations to the signal, by comparing signal data with stored reference profiles, or by other appropriate methods. It has an output 23 provided to a display 24, permitting the glucose level indication to be presented to the user. The output may be directly provided to display 24, or sent remotely via a transmitter. Display 24 may be an alphanumeric display which displays the glucose concentration as a percentage.

The glucose level monitor instrument 10 may also include a medication delivery device, such as insulin pump 26, which is responsive to the glucose level signal or other spectroscopic data or analysis provided by processor 22. A transmitter may be used to transmit the glucose level signal of processor 22 to the pump. The pump is configured so that it converts the glucose level signal received from processor 22 into an insulin dispensing rate. A single bolus of insulin may also be administered based on the glucose level signal. The use of an insulin pump allows the glucose level to be controlled both continuously and automatically. The medication delivery device can also deliver another therapeutic substance, or administer an electrical, chemical, or mechanical stimulus. Miniaturized devices may be constructed of disposable materials such as plastics and paper to further reduce cost. Instrument 10 may be implemented in a number of different ways. It may be implemented at a board level, with the various elements described being separate components, mounted on a circuit board. Many of the elements may also be integrated into a dedicated special-purpose integrated circuit allowing a more compact and inexpensive implementation. Alternatively, the components may be miniaturized further to create an implantable device or a dermal patch. In integrating and miniaturizing the various functions of the instrument, many of them may be combined. Important algorithms may be embedded.

Instrument 10 may also include a normalizing section. The normalizing section is designed to reduce or eliminate the effect of variations, such as the intensity of source 14 or day to day variations in the patient's tissue. A normalizing section may include a second detector that is responsive to a species in the skin that fluoresces but does not respond to glucose concentration. It may also normalize to a signal collected at another time, another site, or another wavelength or from a different internal or external target. Processor 22 may receive signals from the two detectors and derive a normalized glucose level signal. Preferably instrument 10 includes a portable housing bearing ultraviolet radiation source 14, ultraviolet radiation detector 18, acquisition interface 20 and processor 22. Instrument 10 may be powered via battery contacts by a battery contained in the battery compartment located within the housing. Preferably, the entire assembly weighs in combination less than 20 kg, preferably less than 10 kg and more preferably less than 1 kg. Highly portable embodiments which weigh under one kg may be attached to the patient in a monitoring position, such as by an elastic or hook-and-loop fastener strap.

In operation, a physician or the patient places source 14 close to an area of interest on the patient's skin 16. Preferably, this area is one that is not regularly exposed to sunlight, such as the inside of the upper arm. The physician or patient may then start the instrument's monitoring sequence. The monitoring sequence begins with driving circuit 12 producing a driving signal that causes source 14 to irradiate the area of interest on the surface of the skin 16 with one or more bands of ultraviolet radiation. The spectral content of this radiation is selected to cause one or more targets within the skin to fluoresce. These targets may include tryptophan, collagen cross-links or other suitable targets. The excitation/emission wave lengths for tryptophan and collagen cross-links are 295/340–360 nanometers and 335–340/380–400 nanometers, respectively. To increase the sensitivity of the measurement, it is also possible to pre-expose the area of interest with a higher intensity of radiation, before making measurements. Note also that the excitation and emission wavelengths are representative of the molecular species targeted. Under circumstances where the target is responsive to multiple different wavelengths and provides different information from each, or where targets and non-targets are responsive to the same wavelength, more accurate and qualitative values may be obtained by identifying and eliminating background and other interfering data.

The target absorbs the radiation from the source and re-emits it back to detector 18. Detector 18 derives a signal representative of the received emitted radiation and provides it to the acquisition interface 20. Acquisition interface 20 translates the derived signal into a digital value, which it provides to processor 22. Processor 22 converts the digital value into a display signal, which it provides to display 24. The display signal may take the form of an alphanumeric representation which correlates with the concentration of glucose in the blood, or it may include another kind of display signal to be used with another type of display. For example, it is possible to use a color coding scheme to indicate levels of glucose, or indicate dosage amounts to the patient on the display based on the signal received at the detector. The display need not be a visual display; tactile actuators, speakers, or other machine-human interfaces may be employed. The glucose level signal produced by the processor may be directly displayed to indicate the patient's glucose level. Alternately, the processor may first compare the data from the detector with stored reference profiles, such as the patient's prior levels, to provide information regarding trends in the patient's glucose level.

Still another aspect of the invention is related to a glucose monitoring system with alarm features. Parents of children with diabetes are under a continuous threat that a severe hyper- or hypoglycemic event may occur without their knowledge, such as during the night, with potentially fatal consequences. There are an increasing number of individuals with diabetes in need of a device for monitoring their glucose levels. Accordingly, this aspect of the invention is related to a monitoring device with an alarm that alerts a parent or other interested person in the event of large or dangerous changes or trends in the blood glucose levels of a patient. The device reports systemic hyperglycemic and/or hypoglycemic events using fluorescent detection of alterations in the environment of matrix components that reflect changes in blood glucose. Alternately, the device may detect the change in fluorescence from the excitation of another suitable species, such as tryptophan. The device may be completely portable, miniaturized and/or disposable allowing its use in nearly any environment.

The alarm may be any suitable alarm including, but not limited to, a sound alarm or a radio transmitter that activates a sound or light emitting unit in the proximity of the parents or other interested person. The alarm may be audible, visible, vibrating or any other sensory detectible type. For example, in one embodiment, the patient's glucose level is measured once or at a plurality of intervals shortly before the patient goes to sleep to determine a baseline glucose level. The device is programmed to take measurements of the patient's glucose level at periodic intervals during the night, and to then compare these results with the baseline. If the glucose level varies more than a predetermined percentage from the baseline either simply or utilizing specifically designed algorithms, an alarm sounds. Although any desired percentage variation can be selected, in a preferred embodiment, the alarm is activated when the glucose level varies more than 5%, 10%, 20% or more from the previously determined baseline or in accordance with a previously defined set of parameters or specifically designed algorithms. Alternately, or in addition, the alarm is triggered if the patient's blood glucose level exceeds a first predetermined level (i.e. it exceeds 200 gm/ml) or if it falls below a second predetermined level (i.e. it falls below 70 gm/ml). When the alarm sounds, the patient can then be administered insulin (or other suitable medication) if the glucose level is too high, or can be given a source of sugar if the glucose level is too low. Alternatively, or in addition, the alarm may be triggered if other analysis or trending patterns occur.

Optionally, the processor of this device, or any of the monitoring devices disclosed herein, may include means for storing and displaying a plurality of sequential measurements, so that trends which occur during the night or during other time periods of interest may be saved and evaluated. The measurements can be taken continuously or repetitively at predetermined intervals. For example, a patient can be periodically monitored after the administration of one or more of the various forms or sources of insulin (i.e. lente, ultralente, semilente, regular, humalog, NPH etc.) or other glucose regulatory therapies to determine or help to determine the most suitable treatment protocol for the patient. This may be influenced by a comparison to other readings over time, a broader data base, a derivation based on the slope of the change of the signal over time and where on the scale of patient risk a particular assigned glucose might fall.

As mentioned above, the fluorescence signals measured from the excitation of PDCCL and other tissue components are affected by the changes in the scattering properties of the superficial structural matrix. As the electrolyte balance in the micro environment of collagen cross links changes, changes are induced in fluorescence. In addition, the change in electrolytes also produces a change in the local index of refraction and thus a change in the scattering properties. The change in scattering causes a change in the fluorescence.

Figure 10A:
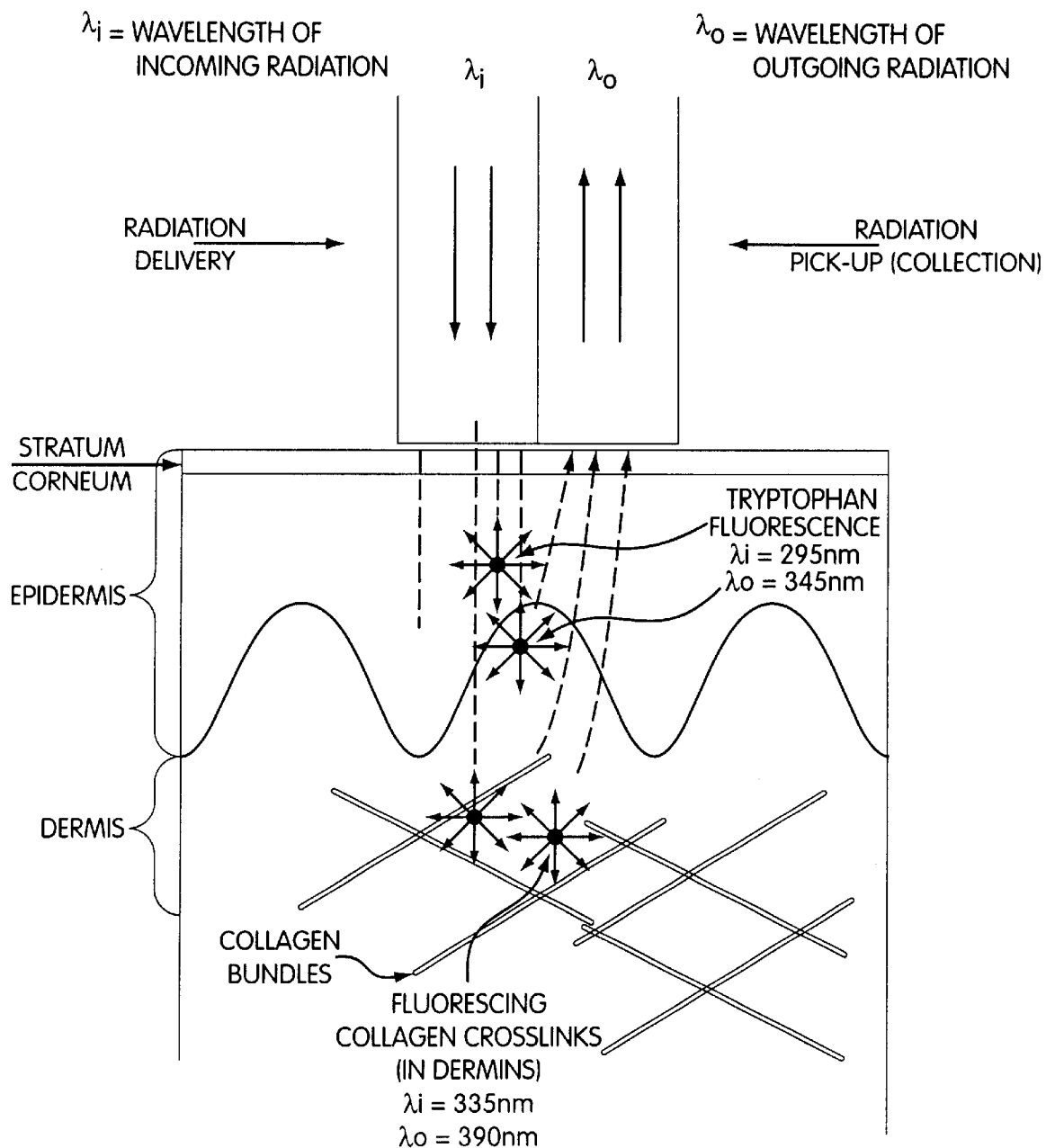
FIG. 10A A diagram depicting collection of fluorescence spectra with components attributable to tryptophan and collagen cross links following irradiation with UV light.

A diagram depicting fluorescence of species sensitive to glucose concentration following irradiation of the skin is depicted in FIG. 10A. Incoming radiation at wavelength $\lambda i$ is directed towards the skin. It penetrates the stratum corneum. If $\lambda i$ is 295 nanometers, fluorescent radiation ($\lambda o$) will be emitted at 345 nanometers by tryptophan in the epidermis of the skin. If $\lambda i$ is 335 nm, fluorescent radiation will be emitted ($\lambda o$) at 390 nm by the collagen cross links in the dermis.

Figure 10B:
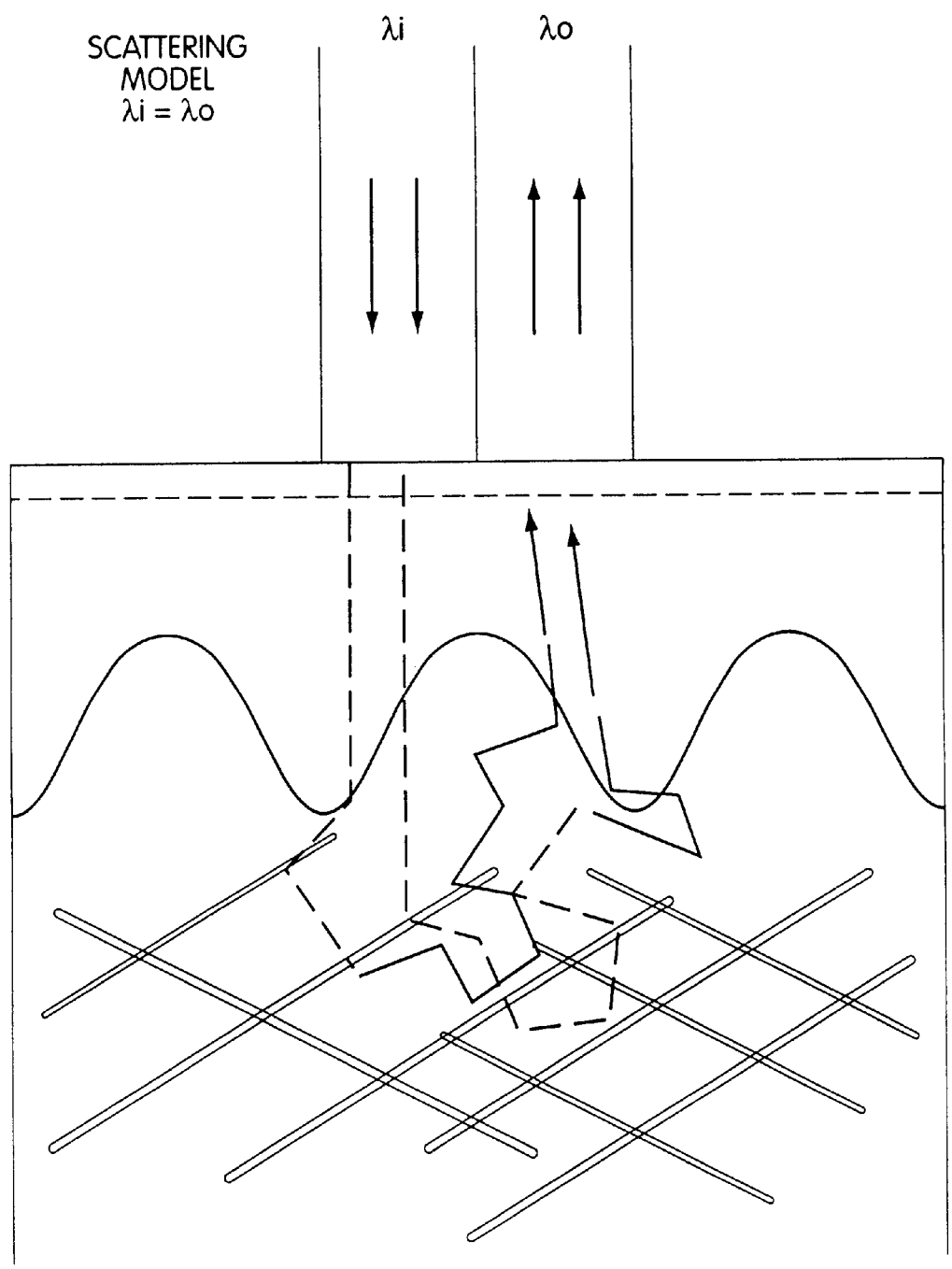
FIG. 10B A diagram depicting scattering according to a scattering model.

A diagram depicting a scattering according to a scattering model is depicted in FIG. 10B which shows collagen cross links in the superficial dermis bending incoming light ($\lambda i$) in different directions. The re-emitted light ($\lambda o$) is at the same wavelength as the incoming light ($\lambda i$), but is scattered due to changes in the local index of refraction. By independently measuring scattering in the superficial matrix, the monitoring of blood glucose levels by measuring fluorescence, as described above, can be enhanced. Specifically, the results from the assessment of scattering can be used to correct for changes in fluorescence induced by changes in the scattering properties of the relevant layers of the dermal matrix.

Accordingly, another aspect of the invention is related to a device that measures the scattering properties of a target such as superficial collagen dermal matrix in the skin, which is affected by changes in the chemical environment which can be correlated with blood glucose levels. Although it has been previously been reported that the scattering properties of the skin (dermal matrix) change with glucose concentration and that these changes are measurable with photon migration techniques in the near infrared (NIR), the use of NIR wavelengths provides a sample of the whole dermis and subcutis (does not measure one signal specific for glucose, but rather many signals that are neither specific for glucose nor reliably linked to glucose levels in a linear fashion). In contrast, the present invention assesses the scattering properties of the superficial dermis, as opposed to the deeper layers. Such scattering of polarized light by the superficial dermal matrix is most noticeable in the range 380–700 nm.

Assessment of scattering in tissue, such as the superficial dermis, associated with changes in blood glucose can most preferably be measured by using short wavelengths (330–420 nm) or launching the illuminating light at large angles (preferably >60°). Short wavelengths are preferably used because they penetrate to a small depth into the dermis. Alternately, changes in scattering induced by the presence of glucose may be measured using light in the visible range of 620–700 nm and looking for changes in signal intensity.

One of the benefits of assessing scattering of the superficial dermis, as opposed to deeper layers of the dermis, is that fluorescent signals from PDCCL's and other matrix components originate there and are affected by the changes in the scattering properties. Further, the superficial layers of the dermis (in areas of the body receiving minimal environmental insults) are well organized and this would be reflected in scattering of polarized light. Since glucose has a strong polarization rotation property, such changes may be measurable when monitoring at a submillimeter resolution, but when monitoring on a gross scale the effects of local organization would be canceled out. Increases in fluorescence may be compensated for by decreases in the effective scattering, making the fluorescence signal difficult to separate from background noise. By independent measurement of the scattering with randomly polarized and with linearly polarized light, fluorescence detection may be enhanced, allowing it to stand on its own merit as a method of indirect measurement of glucose concentration.

Figure 11:
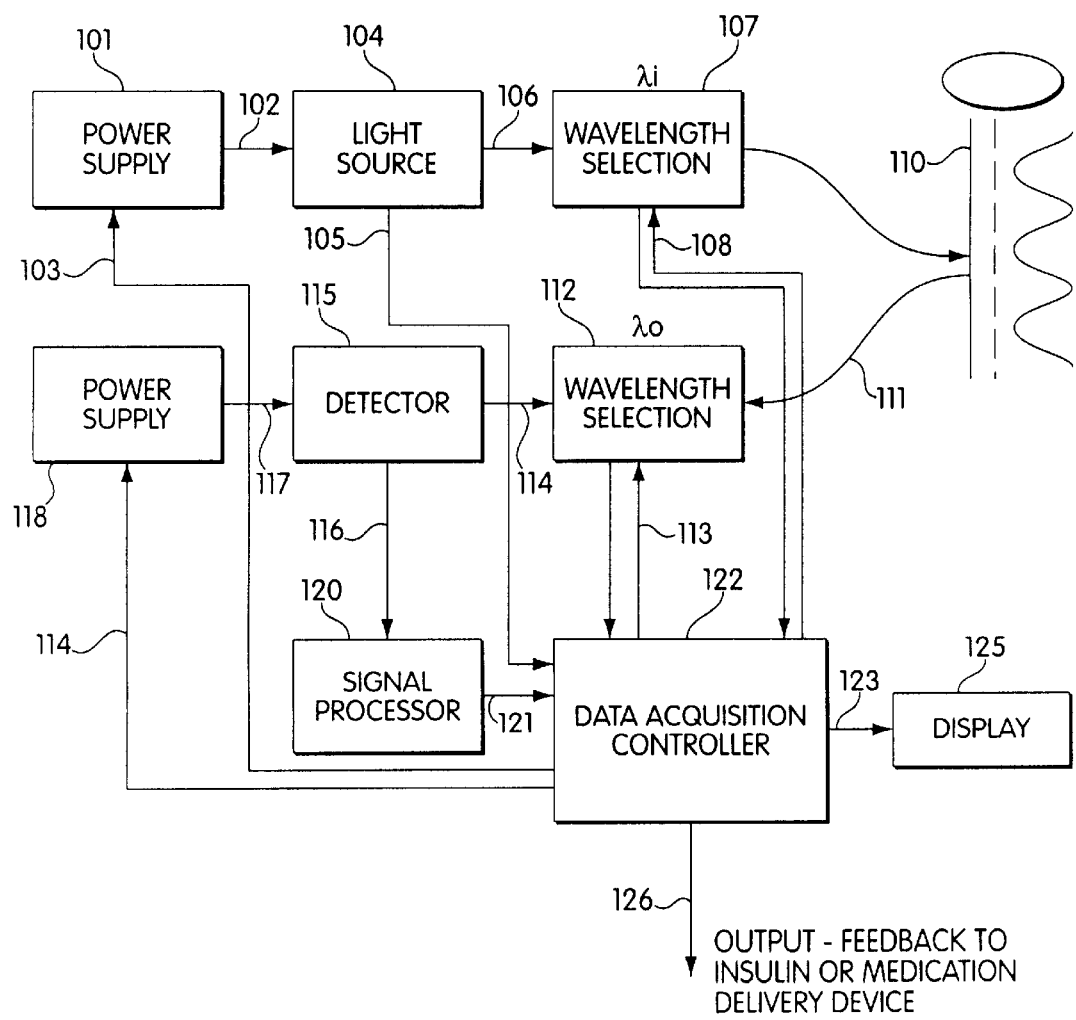
FIG. 11 Block diagram of a monitoring instrument that can be used to monitor tissue glucose levels or evaluate changes in the superficial structural matrix of a tissue or the environment of matrix components of a tissue.

FIG. 11 depicts an embodiment in which both fluorescence of the superficial dermis and scattering are evaluated in order to assess glucose levels. Although this embodiment is described in connection with monitoring blood glucose, as will be clear to those of skill in the art, it can be adapted to assess the status of other analytes, or to detect changes in the superficial structural matrix or matrix components of a tissue. Instrument 100 comprises a power supply 101 connected via connection 102 to a light source 104. Light source 104 may be a lamp, an arc lamp, a laser, or other suitable illumination device. Power supply 101 receives feedback 103 from data acquisition controller 122 to regulate the intensity, synchronization or pulse rate of the light emitted from light source 104. Light source monitor output 105, which may comprise a PIN diode, Avalanche diode, photomultiplier, CCD or other suitable device, couples the light source 104 to data acquisition controller 122. Light 106 is directed to wavelength selection device 107, where an appropriate wavelength is selected, and selected light wavelength output 109 is directed via a fiber, prism or a combination or directly through the air, to illuminate skin 110. Wavelength selection device 107 may comprise a monochromator, a filter or a combination of both. If a laser source is used as light source 104, a filter or other wavelength selection device may not be needed. Wavelength selection device 107 is coupled via signal connection 108 to data acquisition controller 122 to enable selection of the wavelength and to verify the present wavelength.

Fluorescent signals are emitted and scattered light is re-emitted from skin 110. The fluorescent light and reflective intensity 111 is picked up by wavelength selective device 112, which may comprise a monochromator, filter or a combination. Wavelength selective device 112 provides a light output 114 to detector 115. Detector 115 may comprise a photomultiplier, diode, avalanche diode, CCD or other suitable detection device. The signal from detector 115 is transmitted to signal conditioner/processor 120 via signal connector 116. Detector 115 is supplied power via power cable connection 117 from power supply 118. Data acquisition controller 122 provides input to power supply 118 via signal connection 119 to allow selection of sensitivity or synchronization with the light source. Wavelength selection device 112 is coupled via connection 113 to data acquisition controller 122 to select wavelength and verify current wavelength. Signal processor/conditioner 120 provides output via output connection 121 to data acquisition controller 122. Data acquisition controller 122 is connected via connection 123 to display 125. Data acquisition controller 122 may also provide output via connection 124 to an insulin or medication delivery device.

The above described instrument may also be used as a non-invasive device for assessing changes in the superficial structural matrix or the environment of matrix components due to a variety of disease conditions. This embodiment allows the assessment of changes in the structural matrix non-invasively by measuring the combination of fluorescence and scattering, and comparing these results to measurements of developed standards, temporal correlates or surrounding normal tissue. This device may be used to assess changes in the collagen matrix brought about by diseases such as diabetes, scleroderma, scarring, or atrophy induced by the use of steroids. It is also useful to assess changes in the matrix due to aging or photoaging and changes induced by long exposures to zero gravity environment. This embodiment may be miniaturized, and may be used clinically and in research applications to evaluate wound healing, protein metabolism, diabetes, collagen diseases and other conditions.

The collagen cross links in the superficial or papillary dermis provide large fluorescence signals that are indicative of the state of the collagen matrix. These signals may be monitored non-invasively without interference with the functions of the skin. Specifically, as the matrix is irradiated with UVA, UVB or UVC radiation, the fluorescence of PDCCL decreases. This fluorescent effect recovers following a single exposure; however, the changes induced become permanent after multiple exposures.

The fluorescence of the skin in the UVA (320–400 nm) results mainly from collagen cross links that lie in the papillary dermis. The fluorescence signals from these cross links may be used to evaluate the state of the collagen matrix. In the skin and other tissues, as the collagen matrix is degraded due to the expression of matrix metalloproteinases, such as collagenase, in the stroma of tumors so does the fluorescence emission from the collagenase digestible collagen cross links. By assessing fluorescence, it has been discovered that degenerative changes in the superficial structural matrix or of matrix components may be assessed, such as changes induced by disease or environmental factors such as diabetes, age, photodamage, topical steroid application, or prolonged exposure to zero-gravity. Further, the intensity of scattered light by the dermis changes with aging and with changes in the collagen cross links. If the collagen cross links in the superficial or papillary dermis change, then the amount of light that is scattered by the dermis and its dependence on wavelength will also change. These changes may be monitored by reflectance.

Another aspect of the invention is related to a device that can measure either fluorescence excited at about 335 nm (pepsin digestible collagen cross links), fluorescence excited at about 370 nm (collagenase digestible collagen cross links), or both, as well as the reflectance spectrum (450–800 nm), to thereby provide information on the state (or changes induced) of the superficial structural matrix or environment of tissue matrix components. By combining the assessment of fluorescence and scattering into one instrument, a novel device is provided that provides enhanced information on the state of the structural matrix or environment of tissue matrix components. Other wavelengths can also be used for excitation, such as 295 nm for tryptophan. A preferred embodiment incorporates a light source (Hg) and filters to select either 333 nm 365 nm or visible broad band. The visible excitation may be provided by a tungsten halogen lamp of 1–2 watts. The light is then conducted to the skin's surface by fibers, reflective optics or directly, and the fluorescence from the UVA excitations and the reflectance from the visible source are assessed with a photodiode array type of detectors. The fluorescence intensities can then be compared to standard signals from collagen samples (prepared from gelatin). The reflectance signal is analyzed for scattering and absorption by iterative methods at wavelengths of 620–820 nm. Accordingly, another aspect of the invention is related to an instrument for assessing changes in a superficial structural matrix of the skin or the environment of the matrix components of a patient comprising means for measuring fluorescence, and means for measuring scattering.

Another aspect of the invention is related to a non-invasive method of assessing a change in the superficial structural matrix of a tissue or a change in the environment of the matrix components of a tissue comprising exposing the tissue to radiation at a first wavelength, detecting an amount of fluorescence emitted by exposed tissue, exposing the tissue to radiation of a second wavelength, detecting an amount of scattering re-emitted from the exposed tissue, and deriving an indication representative of the change in the superficial structural matrix or environment of the matrix components of the tissue based on of the amount of fluorescence detected and the amount of scattering detected. Preferably, the first wavelength is ultraviolet radiation, or is between about 320 and 420 nm and the second wavelength is between about 330 and 420 nm. Preferably, the tissue is skin.

The following examples are offered to illustrate embodiments of the present invention, but should not be viewed as limiting the scope of the invention.

EXAMPLES

Example 1

Glucose Levels of Diabetic versus Non-Diabetic Mice

Figure 3:
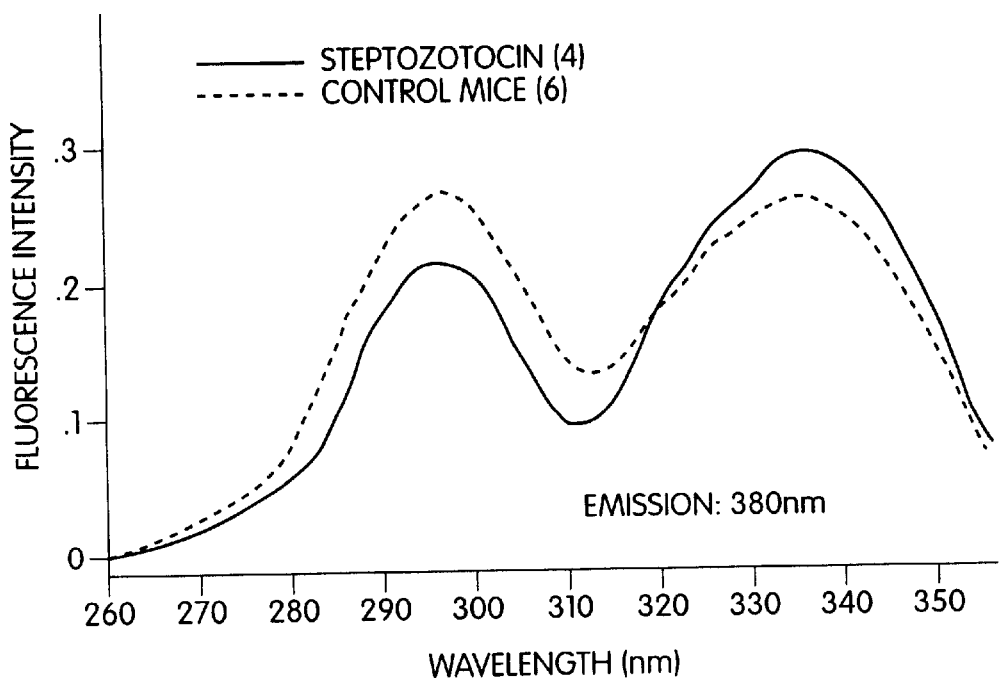
FIG. 3 Graph of the average fluorescence excitation spectra for normal and diabetic SKH mice for an emission wavelength of 380 nm.
Figure 4:
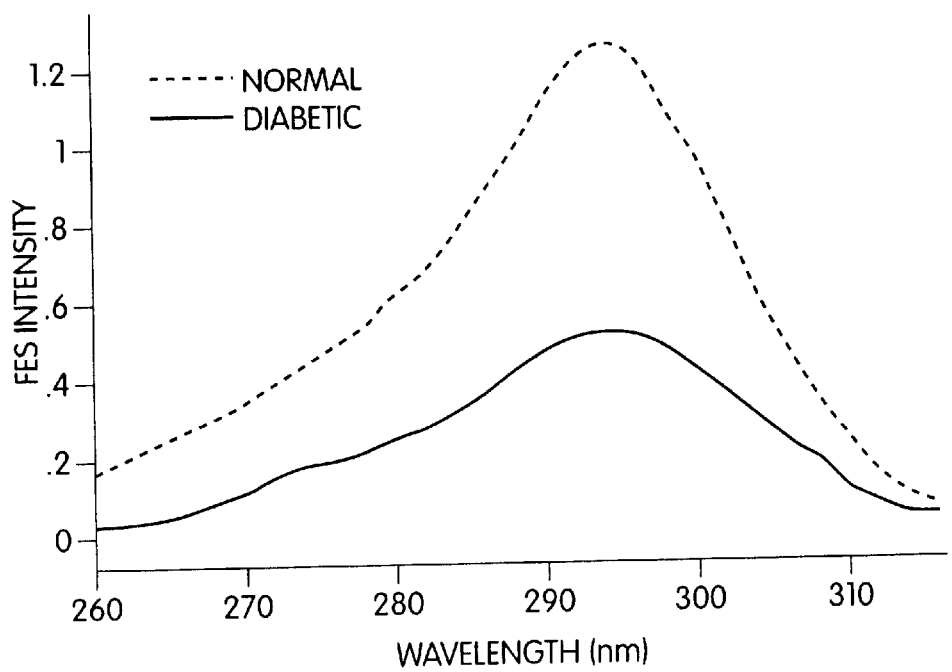
FIG. 4 Graph of the average fluorescence excitation spectra for normal and diabetic SKH mice for an emission wavelength of 340 nm.

Experiments were conducted for six shaved hairless (SKH) diabetic mice made diabetic by the injection of streptozotocin, and six shaved hairless (SKH) non-diabetic (normal) mice. Excitation spectra at emission wavelengths of 380 nm and 340 nm were collected for each of the twelve mice. A Xenon arc source coupled to a monochromator were fed into a fiber optic probe, which was then used to illuminate the backs of all of the mice at an intensity level of approximately 0.1–1.0 mw/cm. A spectrometer was used to collect the resulting spectra, which are shown in FIGS. 3 and 4 for emission at 380 nm and 340 nm, respectively. The plots indicate a significantly lower excitation intensity at 295 nm and a significantly higher excitation intensity at 340 nm for the diabetic mice. Urine collected from the animals confirmed that the glucose levels of the diabetic mice were higher at 340 nm for the diabetic mice.

Example 2

Glucose Levels of a Non-Diabetic Rat Following Ketamine and Insulin Treatments

Figure 5:
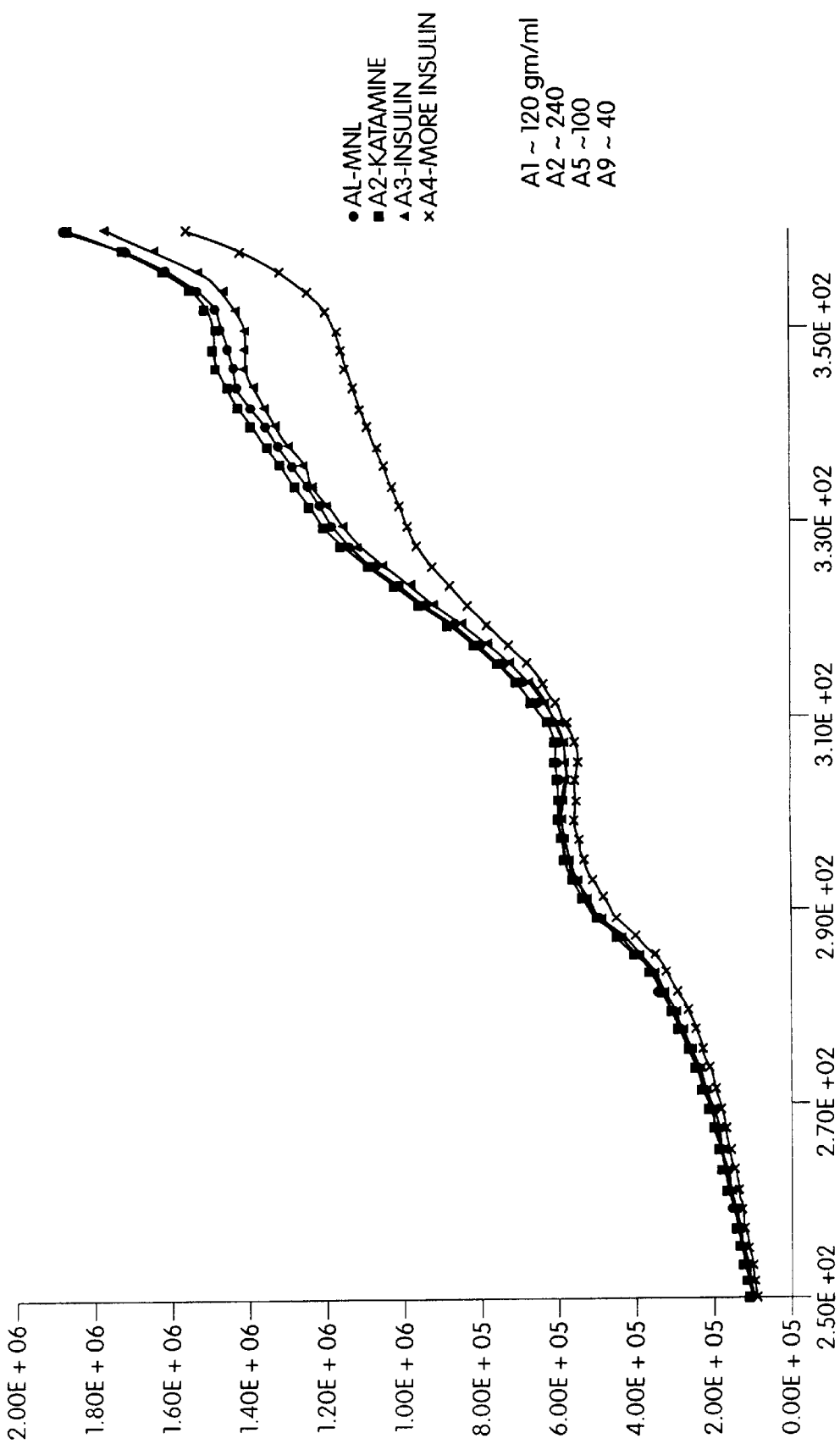
FIG. 5 Graph of the average fluorescence excitation spectra for a rat at an emission wavelength of 380 taken at different blood glucose levels.
Figure 6:
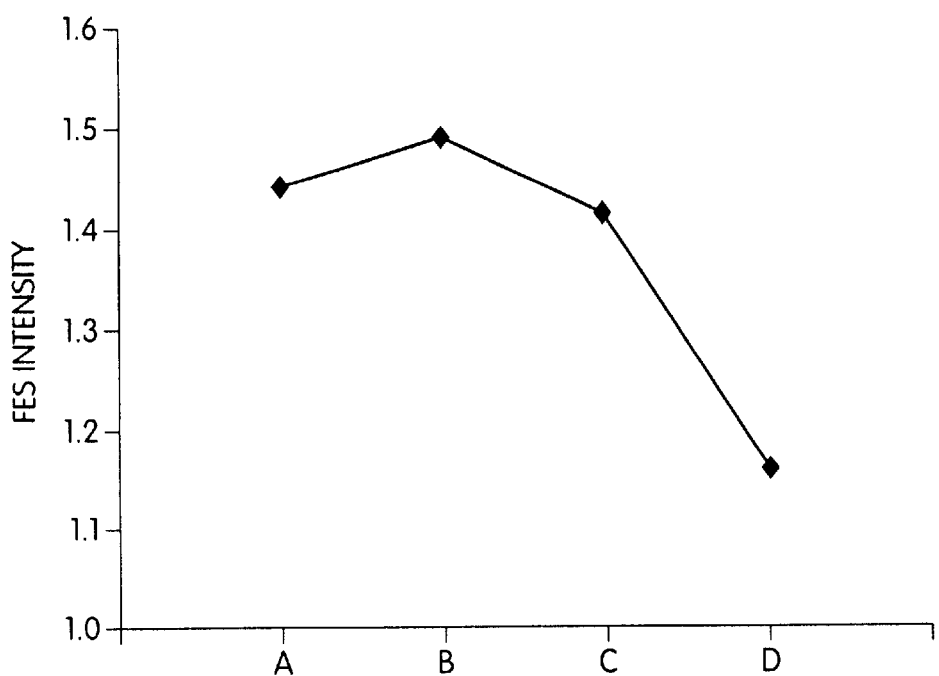
FIG. 6 Plot of the fluorescence intensity at 346 nm for four different glucose levels which are taken from FIG. 5.

Referring to FIG. 5, experiments were also conducted using a normal rat. The experimental apparatus used was the same as that used in Example 1. Fluorescence excitation spectra were obtained for the rat in the following situations, (A) at rest (diamonds), (B) after the administration of Ketamine (squares), (C) after the administration of insulin (triangles) and (D) after the administration of additional insulin (crosses). The glucose levels in situations A–D were determined to be 120, 240, 100, and 40 gm/ml, respectively. The results are believed to be superimposed on a light leakage signal that increases steadily with wavelength, although the use of double monochromators should eliminate this source of background noise. Spectra collected for this rat indicate that blood glucose level has a positive effect on fluorescence excitation in the 340 nm range. This is more clearly depicted in FIG. 6 in which the fluorescence excitation intensity at 346 nm for each of the situations A–D has been plotted.

Example 3

Glucose Levels of Human Subjects Before and After Glucose Ingestion

Figure 7:
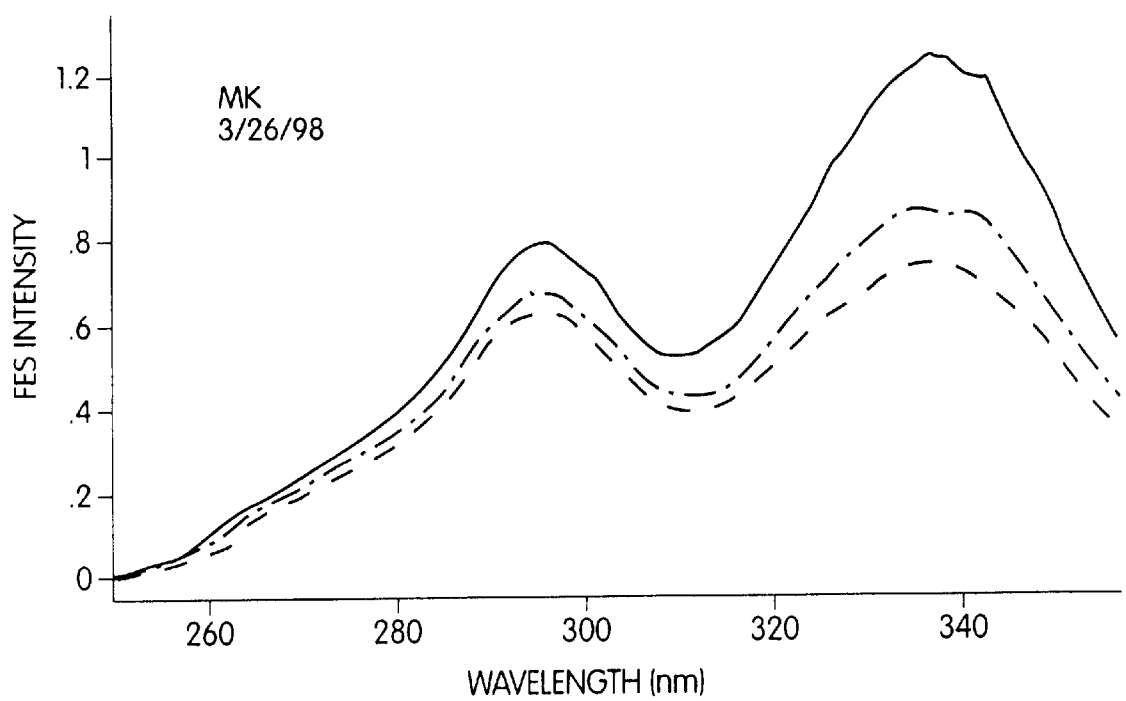
FIG. 7 Graph of the average fluorescence excitation spectra for an emission wavelength of 380 nm for a human male before and after the ingestion of 100 grams of glucose.
Figure 8:
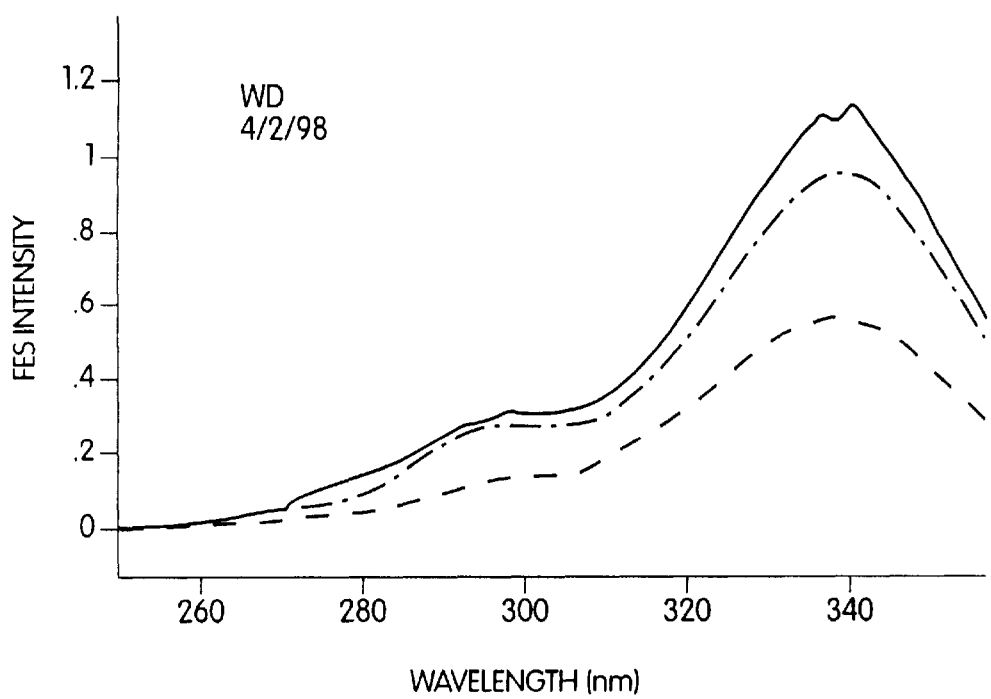
FIG. 8 Graph of the average fluorescence excitation spectra for an emission wavelength of 380 nm for a human male before and after the ingestion of 100 grams of glucose.
Figure 9:
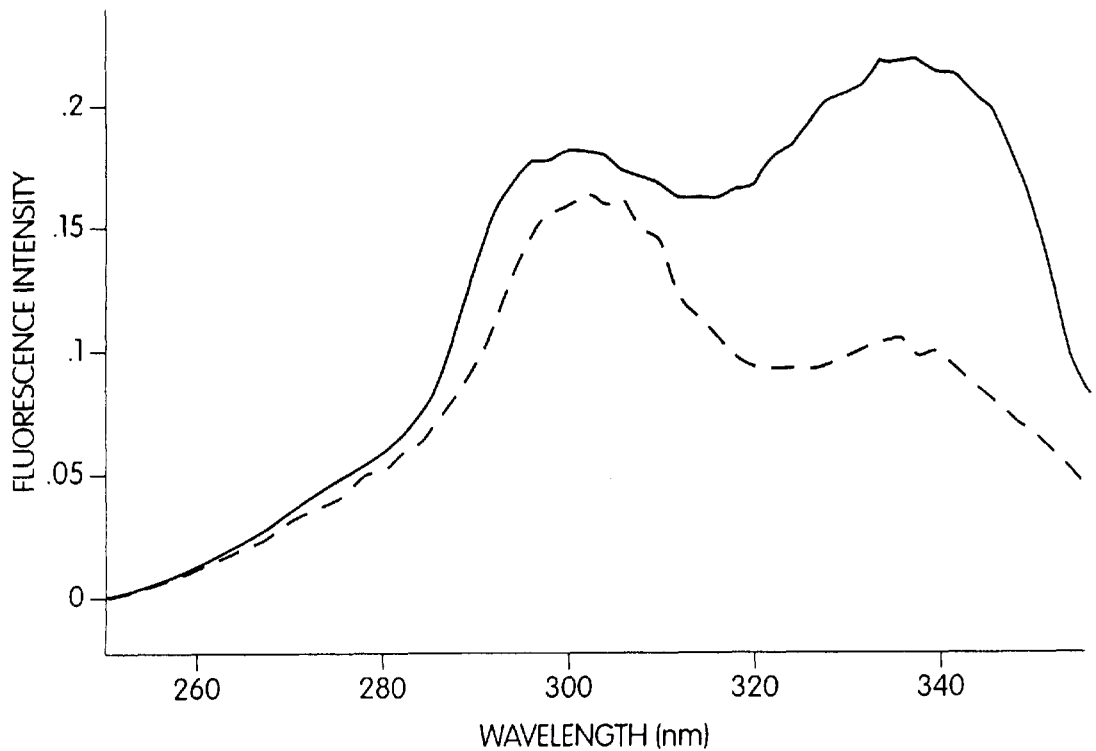
FIG. 9 Graph of the average fluorescence excitation spectra for an emission wavelength of 380 nm for a human female before and after the ingestion of 100 grams of glucose.

Preliminary experiments were also conducted on humans. FIGS. 7, 8 and 9 depict fluorescence excitation spectra for three human subjects, two males and one female, respectively, before (dashes), 30 minutes after (dotted/dashed line), and 60 minutes after (solid line) the ingestion of 100 grams of glucose. In each situation, the emission monochromator was set to a wavelength of 380 nm. Collagen and tryptophan spectra were found to change in ways similar to those for the animal models, although there appear to be individual differences. Dashed lines represent measurements before glucose intake. Dashed and dotted lines represent changes induced after glucose intake. Solid lines represent maximal changes induced by the intake of glucose.

Other embodiments and uses of the invention will be apparent to those skilled in the art from consideration of the specification and practice of the invention disclosed herein. As will be clear to those of skill in the art, the devices and methods of the present invention can be easily adapted to reflect or detect the level of a variety of substances in tissue, in addition to glucose and the described targets. All references cited herein, including all U.S. and foreign patents and patent applications, including, but not limited to, U.S. Provisional Patent Application Serial No. 60/080,794, entitled Non-Invasive Tissue Glucose Level Monitoring, filed Apr. 6, 1998, are specifically and entirely incorporated by reference. The specification and examples should be considered exemplary only with the true scope and spirit of the invention indicated by the following claims.

We claim:

1. A nocturnal glucose monitor, comprising:

a non-invasive glucose measurement probe for detecting glucose levels of a juvenile patient, an alarm unit responsive to the glucose measurement probe, the alarm unit being operative to detect excursions of glucose values outside of a predetermined juvenile nocturnal glucose range for a diabetic patient and to produce a parental alarm signal in response to detected excursions, an audio transducer responsive to the alarm signal, and a remote transmitter responsive to the non-invasive glucose measurement probe and a receiver responsive to the remote transmitter, wherein the audio transducer is responsive to the remote transmitter.

2. The nocturnal glucose monitor of claim 1 wherein the remote transmitter is a wireless transmitter and the receiver is a wireless receiver.

3. The nocturnal glucose monitor of claim 2 wherein the glucose measurement probe is a fluorescence-based probe.

4. The nocturnal glucose monitor of claim 1 wherein the glucose measurement probe is a fluorescence-based probe.

5. A nocturnal glucose monitoring method, comprising:

providing a non-invasive glucose measurement probe such that it is responsive to a glucose level of a child during nighttime sleep, detecting excursions of glucose values outside of a predetermined nocturnal glucose range for a diabetic child during nighttime sleep of the child, and causing a remote receiver to issue an audible alarm to a parent of the child in response to the step of detecting.

6. The method of claim 5 wherein the step of causing operates based on wireless transmission.

7. The method of claim 6 wherein the step of detecting operates based on fluorescence.

8. The method of claim 5 wherein the step of detecting operates based on fluorescence.

* * * * *